United States Patent
Ohsaki et al.

(10) Patent No.: US 6,548,662 B1
(45) Date of Patent: Apr. 15, 2003

(54) METHOD FOR PURIFICATION OF SACCHARIDE

(75) Inventors: Shigemitsu Ohsaki, Kashihara (JP); Masao Tamura, Yokohama (JP); Takahisa Yamaura, Yokohama (JP)

(73) Assignees: Sanwa Kosan Kabushiki Kaisha, Kashihara (JP); Nippon Rensui Company, Tokyo (JP)

( * ) Notice: Subject to any disclaimer, the term of this patent is extended or adjusted under 35 U.S.C. 154(b) by 26 days.

(21) Appl. No.: 09/693,373

(22) Filed: Oct. 19, 2000

(51) Int. Cl.$^7$ .............................. C07H 1/06; C07H 1/08
(52) U.S. Cl. ........................................ 536/128; 536/127
(58) Field of Search ................................... 536/127, 128

(56) References Cited

U.S. PATENT DOCUMENTS

| | | | |
|---|---|---|---|
| 4,313,015 A | * 1/1982 | Broughton | 585/828 |
| 4,752,579 A | 6/1988 | Arena et al. | 435/99 |

FOREIGN PATENT DOCUMENTS

| EP | 0 279 946 A2 | 8/1988 |
|---|---|---|
| EP | 0 342 629 A1 | 11/1989 |
| EP | 0 560 284 A1 | 9/1993 |
| JP | 6-170112 | 6/1994 |
| JP | 7-242551 | 9/1995 |
| JP | 9-299093 | 11/1997 |

* cited by examiner

Primary Examiner—Dwayne C. Jones
(74) Attorney, Agent, or Firm—Kolisch Hartwell, P.C.

(57) ABSTRACT

Disclosed herein is a method for the purification of a saccharide, characterized in that, water and a feedstock solution containing at least L-arabinose and oligosaccharide where L-arabinose and/or xylose are/is the constituting component(s) obtained by hydrolysis of plant tissues are supplied to a chromatographic apparatus of a simulated moving-bed system where a solution can be circulated in one direction in an apparatus equipped with a packed bed in which an adsorbent is filled and the solution in the packed bed is moved in one direction whereupon at least L-arabinose and oligosaccharide are separated each other and concentration distribution of each of them is formed in the packed bed, then at least a concentrated L-arabinose solution and a concentrated oligosaccharide solution are extracted from the packed bed and, in addition, an inlet for the feedstock solution, an inlet for water, an outlet for the concentrated L-arabinose solution and an outlet for the concentrated oligosaccharide solution are successively shifted to the downstream inlets or outlets along the flowing direction of the solution.

16 Claims, 2 Drawing Sheets

METHOD FOR PURIFICATION OF SACCHARIDE

FIELD OF THE INVENTION

The present invention relates to a method for the preparation of an L-arabinose solution of a high purity by means of chromatography from a solution containing L-arabinose obtained by hydrolysis of plant tissues.

BACKGROUND ART

Plant tissues are mostly composed of cellulose, hemicellulose, lignin and the like and L-arabinose and D-xylose are included in the monosaccharide which constitutes hemicellulose. Although the content of L-arabinose varies depending upon the plant tissues, it has been known that L-arabinose is contained in large quantities in some kinds of plant tissues such as husk of corn grains, ear of stem of corn, bran of wheat and related vegetables, rice bran, squeezed lees of sugar beet and squeezed lees of apple.

Usefulness of L-arabinose in view of its physiological functions has been reported (cf. Japanese Patent Laid-Open Nos. 06/65080 and 07/242551) and the manufacture of L-arabinose by hydrolysis of plant tissues has been investigated (cf. Japanese Patent Laid-Open Nos. 01/312997 and 09/299093). Recently, there has been developed a method for the manufacture of L-arabinose in an industrial scale by hydrolysis of plant tissues containing 10% by weight or more L-arabinose based on dry materials such as husk of corn grains using an acid of as diluted as 0.01–0.5N at 80–150° C. (Japanese Patent Application No. 10/137485).

SUMMARY OF THE INVENTION

A solution obtained by hydrolysis of plant tissues contains D-xylose in addition to L-arabinose, oligosaccharide such as xylo-oligosaccharide and arabino-xylo-oligosaccharide wherein L-arabinose and/or xylose are/is constituting components (hereinafter, referred to as "oligosaccharide") and glucose. Therefore, for an object of effective utilization of L-arabinose, it is desirable to remove such impurities and to prepare L-arabinose of a high purity. The present invention is to meet with such a demand.

In accordance with the present invention, water and a feedstock solution containing at least L-arabinose and oligosaccharide obtained by hydrolysis of plant tissues are supplied to a chromatographic apparatus of a simulated moving-bed system where a solution can be circulated in one direction in an apparatus equipped with a packed bed in which an adsorbent is filled and the solution in the packed bed is moved in one direction whereupon at least L-arabinose and oligosaccharide are separated each other and concentration distribution of each of them is formed in the packed bed. From such a concentration distribution, at least a concentrated L-arabinose solution and a concentrated oligosaccharide solution are extracted from the packed bed and, in addition, a part where their separation is insufficient is made existed at all times whereupon an L-arabinose solution of high purity can be prepared in a high yield.

Figure 1:
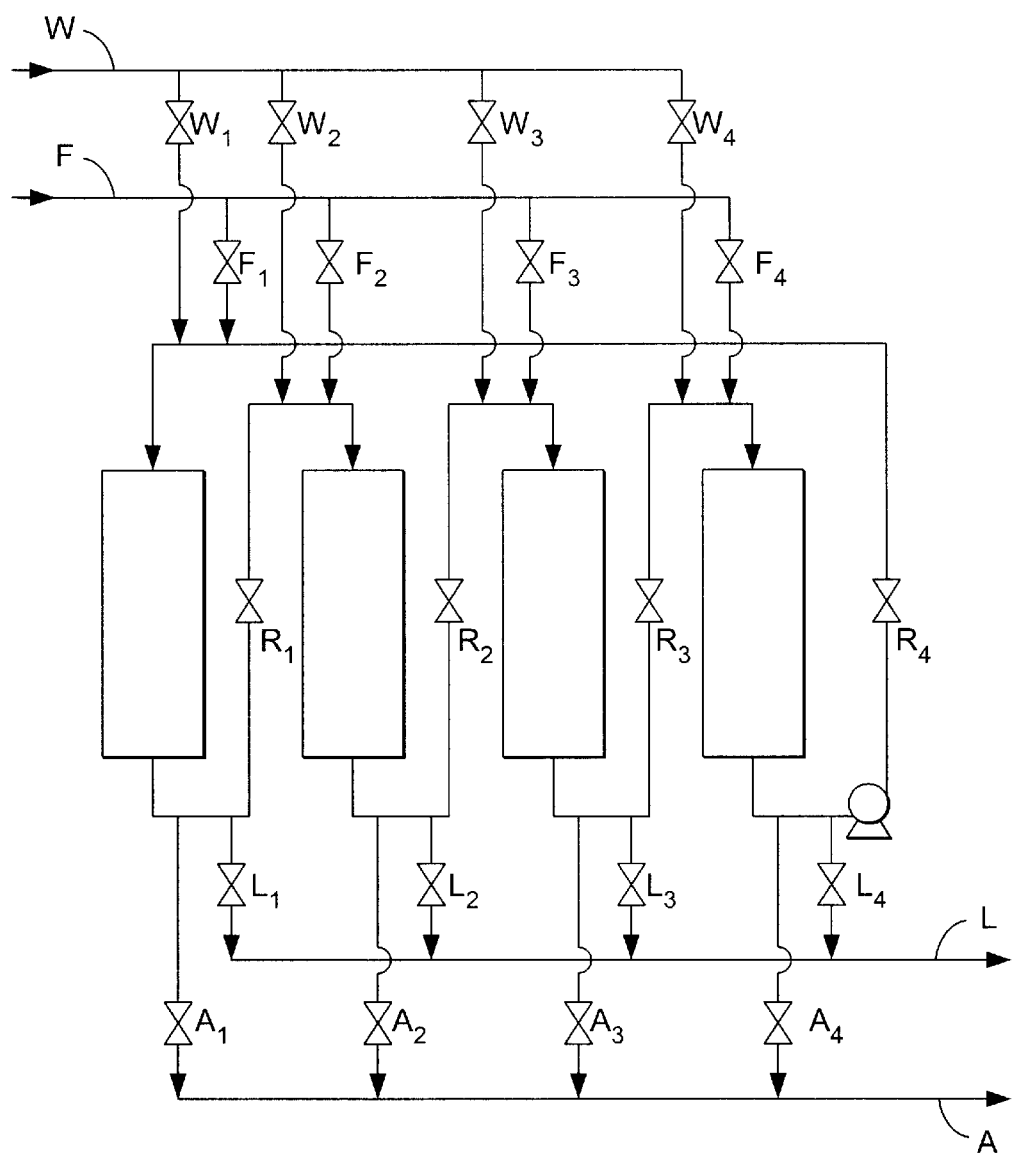
FIG. 1 is an example of a chromatographic apparatus of a simulated moving-bed system for carrying out the present invention and FIG. 2 is an example of a semi-continuous chromatographic apparatus for carrying out the present invention.

In the drawings, W is a pipe for supplying the water, F is a pipe for supplying the feedstock solution, L is a pipe for extracting the oligosaccharide solution, A is a pipe for extracting the L-arabinose solution, X is a pipe for extracting the xylose solution, $W_1$~$W_4$ are valves, $F_1$~$F_4$ are valves, $L_1$~$L_4$ are valves, $A_1$~$A_4$ are valves and $R_1$~$R_4$ are valves.

DESCRIPTION OF THE PREFERRED EMBODIMENTS

In the present invention, a solution in which L-arabinose is concentrated to a high purity (hereinafter, referred to as "L-arabinose solution") is prepared by means of chromatography from a feedstock solution containing L-arabinose, D-xylose and oligosaccharide obtained by hydrolysis of plant tissues. With regard to the plant tissues, it is preferred to use those which contain large amount of L-arabinose as mentioned already. With regard to hydrolysis, it is preferred to use an acid of as diluted as 0.01–0.5N at 80–150° C. as disclosed in Japanese Patent Application No. 10/137485. Composition of the resulting hydrolyzed liquid varies depending upon the plant tissues used for the hydrolysis. It also varies depending upon the hydrolyzing rate and, in general, the amount of L-arabinose and oligosaccharide increases when the hydrolyzing rate is low while, when the hydrolyzing rate becomes high, the amount of L-arabinose and D-xylose increases and that of oligosaccharide decreases. Thus, as the hydrolysis proceeds, oligosaccharide is hydrolyzed and L-arabinose and X-xylose are produced.

In the present invention, a hydrolyzed liquid of any composition may be used as a feedstock solution although the use of a hydrolyzed liquid containing high amount of L-arabinose is preferred. Usually, the liquid where the ratio of L-arabinose to the solid in the feedstock solution is 10% by weight or more is used. It is preferred that the ratio of L-arabinose in monosaccharide in the feedstock solution is 50% by weight or more. The higher the ratio of L-arabinose contained in monosaccharide, the easier the recovery of L-arabinose of high purity in high yield by chromatography.

With regard to an adsorbent for chromatography, any adsorbent having stronger affinity to L-arabinose than to oligosaccharide may be used. Usually, a strongly acidic cation-exchange resin of a salt form, particularly a sulfonated styrene-divinylbenzene cross-linking copolymer, made into an alkaline earth metal salt or, preferably, a calcium salt is used. When such an adsorbent is used, it is also possible that the feedstock solution is separated into the three components, i.e. L-arabinose, D-xylose and oligosaccharide.

With regard to a chromatographic system, a continuous or a semi-continuous system in which the part where separation is insufficient among the components in the feedstock solution supplied to a packed bed is always made existed in the packed bed is preferred over a batch system in which the feedstock solution is supplied from the upper end of the packed bed filled with an adsorbent and water is supplied from the same upper end whereby the components in the feedstock solution are separated into each component and, at the same time, all of the supplied feedstock is extracted from the lower end of the packed bed. Decision of what system is specifically adopted depends upon the object that in what manner the feedstock solution is to be separated. When the feedstock solution is to be separated into an L-arabinose solution and a solution in which oligosaccharide and other components are concentrated (hereinafter, referred to as "oligosaccharide solution"), it is preferred to use a simulated moving-bed system. As being well known, in the simulated moving-bed system, an apparatus in which front and rear ends of the packed bed are connected by a flow pass of the solution whereby the solution can be circulated in the apparatus is used. The packed bed is equipped with an inlet for supplying the feedstock solution, an outlet for extracting a concentrated solution of the components having weak affinity to the adsorbent, an inlet for supplying the water and an outlet for extracting a concentrated solution of the components having strong affinity to the adsorbent in this order along the flow of the solution so that, as the concentration distribution of each component formed in the packed bed moves, the operating inlet and outlet are periodically shifted to the inlet and outlet at immediately down stream where the inlet and outlet still keep the relationship in terms of their relative positions.

When a strongly acidic cation-exchange resin of a calcium form is used as an adsorbent and a hydrolyzed liquid of plant tissues is used as a feedstock solution, an L-arabinose solution is obtained as a concentrated solution of the components having a strong affinity to the adsorbent and an oligosaccharide solution is obtained as that having a weak affinity thereto.

The packed bed of the simulated moving-bed is divided into four zones depending upon its functions, i.e. an adsorption zone occupying the part between an inlet for supplying the feedstock solution and an outlet for the solution of concentrated components having weak affinity, a purification zone occupying the part between the outlet and an inlet for water, a desorption zone occupying the part between an inlet for water and an outlet for the solution of concentrated components having strong affinity and a concentration zone occupying the part between the outlet and an inlet for the feedstock solution. Together with a shifting of the operating inlets and outlets, the four zones successively move in a downstream direction.

The present invention may also be carried out by a standard simulated moving-bed system or, in other words, a solution is always circulated in a packed bed whereby the components are separated each other and a feedstock solution and water are supplied to this circulating flow and, at the same time, a part of the circulating flow is extracted from each outlet although it is preferred to conduct a system where separation of the components by means of circulation of the solution, supplying of the feedstock solution and water and extracting of the oligosaccharide solution and the L-arabinose solution are carried out separately. Such a system has been known and, in its representative one (Japanese Patent Laid-Open No. 02/49159), a process consisting of a supplying and extracting step where the feedstock solution and water are supplied from each supplying inlet to a packed bed and a part of the solution arriving at the position of the outlet for the L-arabinose solution is extracted from the packed bed while all of the solution arriving at the position of the outlet for the oligosaccharide solution is extracted from the packed bed and a circulation step where the solution in the packed bed is moved downstream without supplying the feedstock solution and water to the packed bed and extracting of the solution from the packed bed is carried out and then the above process is repeated after the operating inlet and outlet are shifted to the downstream inlet and outlet together with keeping the relationship for their relative positions.

As a result of repeating a process consisting of a supplying and extracting step and a circulation step and a shifting of the operating inlet and outlet as such, the feedstock solution can be separated into an L-arabinose solution and an oligosaccharide solution. According to such a method, it is possible to achieve a good separating result even when an apparatus which is as simple as a simulated moving-bed system consisting of four unit packed beds is used. Incidentally, in a method where the feedstock solution is separated into two, i.e. an L-arabinose solution and an oligosaccharide solution, D-xylose and D-glucose in the feedstock solution are contained in both of the L-arabinose solution and the oligosaccharide solution and are extracted. Generally, D-glucose is present in an oligosaccharide solution in higher concentration while D-xylose is present in an L-arabinose solution in higher concentration.

In another embodiment of the present invention, the feedstock solution is separated into three, i.e. a solution where D-xylose is concentrated (hereinafter, referred to as "D-xylose solution) in addition to an L-arabinose solution and an oligosaccharide solution. Accordingly, when L-arabinose of a high purity is to be prepared from a feedstock solution where the ratio of D-xylose in the weight of dry substance is high, it is preferred to use the above embodiment.

With regard to a method of separation of the feedstock solution into an L-arabinose solution, a D-xylose solution and an oligosaccharide solution, a system which is similar to the above-mentioned one where a supplying and extracting step and a circulating step are combined as in such a system mentioned in Japanese Patent Laid-Open No. 06/170112 may be used. In the said system, outlets for each of an L-arabinose solution, a D-xylose solution and an oligosaccharide solution are prepared on the packed bed. The separating operation is that a process consisting of a step where the feedstock solution or water is supplied to a packed bed and a concentrated solution of any of the components is extracted from the packed bed and a step where the solution in the packed bed is moved downstream without supplying of the liquid to the packed bed and extracting of the solution from the packed bed is repeated together with a successive shifting of the operating inlet and outlet to a down stream.

Principally, the feedstock solution and water are supplied to the packed bed at the different time in this system. Fundamentally, one process of this operating method consists of the following steps.

(a) a step of supplying the feedstock solution where the feedstock solution is supplied from an inlet for the feedstock solution to move the solution in the packed bed downstream and all of the solution arriving at the position of the outlet for a D-xylose solution is extracted as a D-xylose solution;

(b) a circulation step where the solution in the packed bed is moved downstream in a circulating manner without carrying out supplying and extracting; and (c) a desorption step comprising the following substeps (i) and (ii):
  (i) water is supplied from the inlet for water to move a solution in the packed bed downstream, a part of a solution arriving at the position of outlet for an L-arabinose solution is extracted as an L-arabinose solution and all of the solution arriving at the position of outlet for an oligosaccharide solution is extracted as an oligosaccharide solution and
  (ii) a solution in the packed bed is moved downstream in a circulating manner without supplying and extracting.

Incidentally, the desorption step is repeated until the concentration distribution of each component in the packed bed becomes the same as that at the initiation stage of the process by means of shifting of the operating inlet and outlet to the downstream inlet and outlet successively within a step. When the amount of the D-xylose solution extracted in the step of supplying the feedstock solution does not reach the desired amount, it is also possible that water is supplied to the supplying position for water in the packed bed after supplying the feedstock solution and all of the solution arriving at the position of the outlet for a D-xylose solution is additionally extracted as a D-xylose solution.

As to another method for separating the feedstock solution into an L-arabinose solution, a D-xylose solution and an oligosaccharide solution, a method disclosed in Japanese Patent Laid-Open No. 63/158105 may be used as well. Fundamentally, this method consists of the following five steps. Thus, a step (I) where the feedstock solution is supplied from the upper end of the packed bed and a D-xylose solution is extracted from the lower end;

a step (II) where neither supplying nor extracting is carried out but a solution in the packed bed is moved from the lower end of the packed bed to the upper end thereof so that the solution is moved in the packed bed in a circulating manner;

a step (III) where water is supplied from the upper end of the packed bed and an L-arabinose solution is extracted from the lower end of the packed bed;

a step (IV) where water is supplied from the upper end of the packed bed and an oligosaccharide solution is extracted from the lower end of the packed bed; and a step (V) where the solution in the packed bed is moved from the lower end of the packed bed to the upper end thereof without carrying out the supplying and the extracting so that the solution is moved in the packed bed in a circulating manner.

Even in this method, there is a relationship that the supplying amount of the feedstock solution is equal to the extracted amount of the D-xylose solution and, therefore, when the extracted amount of the D-xylose solution does not reach the desired amount, it is possible to carry out an additional extracting step (I') where water is supplied from the middle of the packed bed after the step (I) so that a D-xylose solution is extracted from the lower end.

In any of the systems, it is preferred that the feedstock solution is supplied in a state of as concentrated as possible and that both feedstock solution and water are supplied to the packed bed at the temperature of as high as possible (60° C. at the lowest) so as to lower the viscosity of the solution in the packed bed.

Further, in order to prevent the deterioration of the adsorbent, it is preferred that the feedstock solution is supplied after being desalted. The supplying amount of water to the feedstock solution varies depending upon the system and, in case two kinds of solutions—an L-arabinose solution and an oligosaccharide solution—are extracted from the packed bed, 2- to 4-fold of water to the feedstock solution is usually supplied.

When three kinds of solutions—an L-arabinose solution, a D-xylose solution and an oligosaccharide solution—are extracted from the packed bed, 3- to 7-fold of water to the feedstock solution is usually supplied. Thus, when three kinds of solutions are extracted, they are usually diluted as compared with the case where two kinds of solutions are extracted.

In accordance with the present invention, a solution of L-arabinose in a purity of at least 75% by weight can be easily prepared from the feedstock solution and, further, it is not difficult to prepare a solution of L-arabinose in a purity of 90% by weight or more.

Purity of an oligosaccharide in a concentrated oligosaccharide solution separated from the feedstock solution is at least 75% by weight or preferably 90% by weight or more while purity of D-xylose in a concentrated D-xylose solution separated from the feedstock solution is at least 70% by weight or preferably 80% by weight or more.

The present invention will now be more specifically illustrated by way of the following examples although the present invention is not limited by such examples.

EXAMPLE 1

The feedstock solution prepared by hydrolysis of plant tissues using a simulated moving-bed of FIG. 1 was separated into an L-arabinose solution and an oligosaccharide solution.

The simulated moving-bed was composed of four unit packed beds each having an inner diameter of 27 mm and a packed layer height of 550 mm and was equipped with a pipe (F) for supplying the feedstock solution, a pipe (W) for supplying the water, an outlet pipe (A) for an L-arabinose solution and an outlet pipe (L) for an oligosaccharide solution.

Cation-exchange resin of a calcium form (in a gel type; average particle size: 220 $\mu$m) was filled in each unit packed bed.

The separating operation was carried out as follows. Thus, a process consisting of a supplying and extracting step for 9 minutes where the feedstock solution and water were supplied to the simulated moving-bed at 65° C. and an L-arabinose solution and an oligosaccharide solution were extracted and a circulating step for 12–13 minutes where the inner solutions were moved in a circulating manner without supplying and extracting was repeatedly carried out together with a successive shifting of the inlet and the outlet to the corresponding inlet and outlet of the unit packed bed which were immediately downstream. Accordingly, when the process was repeated for four times, the state returned to the original one. Supplying speed of the feedstock and water and extracting speed of the concentrated solutions in the supplying and extracting step and the flow rate (flow rate of the liquid sent by a circulation pump) of the circulating liquid in the circulating step were as follows.

| | |
|---|---|
| Feedstock Solution | 233 ml/hr |
| Water | 600 ml/hr |
| L-Arabinose Solution | 293 ml/hr |
| Oligosaccharide Solution | 540 ml/hr |
| Circulating Liquid | 600 ml/hr |

State of opening and closing of the valve as a result of repetition of the process for four times until the apparatus returned to the initial state was as shown in the following Table 1. In Table 1, "○" is a state where the valve was open while "×" is a state where the valve was closed. Composition of the feedstock solution and compositions of an L-arabinose solution and an oligosaccharide solution at a stationary state are as shown in Table 2.

TABLE 1

| Pr | St | Supplying Valve for Feedstock Solution | | | | Supplying Valve for Water | | | | Extracting Value for L-Arabinose | | | | Extracting Valve for Oligosaccharide | | | | Circulating Valve | | | |
|---|---|---|---|---|---|---|---|---|---|---|---|---|---|---|---|---|---|---|---|---|---|
| | | $F_1$ | $F_2$ | $F_3$ | $F_4$ | $W_1$ | $W_2$ | $W_3$ | $W_4$ | $A_1$ | $A_2$ | $A_3$ | $A_4$ | $L_1$ | $L_2$ | $L_3$ | $L_4$ | $R_1$ | $R_2$ | $R_3$ | $R_4$ |
| 1 | SE | O | X | X | X | X | X | O | X | X | X | O | X | O | X | X | X | X | O | O | O |
| | C | X | X | X | X | X | X | X | X | X | X | X | X | X | X | X | X | O | O | O | O |
| 2 | SE | X | O | X | X | X | X | X | O | X | X | X | O | X | O | X | X | O | X | X | O |
| | C | X | X | X | X | X | X | X | X | X | X | X | X | X | X | X | X | O | O | O | O |
| 3 | SE | X | X | O | X | O | X | X | X | O | X | X | X | X | X | O | X | O | O | X | X |
| | C | X | X | X | X | X | X | X | X | X | X | X | X | X | X | X | X | O | O | O | O |
| 4 | SE | X | X | X | O | X | O | X | X | X | O | X | X | X | X | X | O | X | O | O | X |
| | C | X | X | X | X | X | X | X | X | X | X | X | X | X | X | X | X | O | O | O | O |

Pr: Process; St: Step; SE: Supplying and Extracting; C: Circulating

TABLE 2

| | Composition (% by weight) | | |
|---|---|---|---|
| | Feedstock Solution | L-Arabinose Solution | Oligosaccharide Solution |
| L-Arabinose | 28.1 | 92.8 | 1.5 |
| D-Xylose | 4.2 | 6.7 | 3.2 |
| Glucose | 1.7 | 0.2 | 2.3 |
| Oligosaccharide | 66.0 | 0.3 | 93.0 |
| Concn of Solid (wt %) | 60.0 | 16.5 | 21.4 |

EXAMPLE 2

Figure 2:
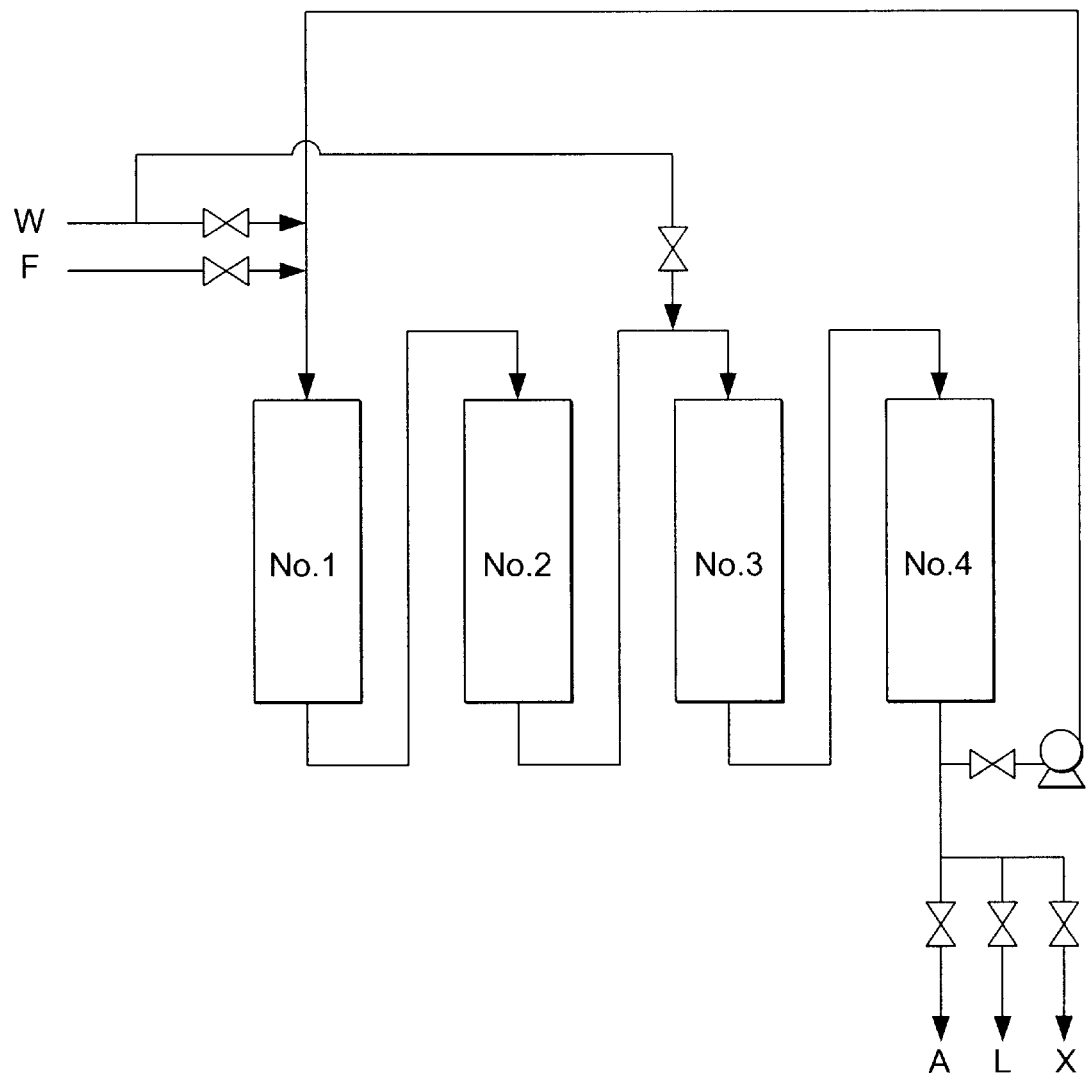

The feedstock solution obtained by hydrolysis of plant tissues using the chromatographic apparatus of FIG. 2 was separated into an L-arabinose solution, a D-xylose solution and an oligosaccharide solution. The apparatus was constituted in such a manner that four unit packed beds (No.1 to No.4) each having an inner diameter of 27 mm and a packed layer height of 550 mm were connected in series and that the lower end of the bed No.4 and the upper end of the bed No.1 were connected by a pass for the solution so that the solution was able to be circulated in the apparatus. Each of the unit packed beds was filled with a cation-exchange resin of a calcium form (gel type; average particle size: 220 $\mu$m)

The separating operation was carried out by repeating the process comprising the following six steps.

First step: The feedstock solution was supplied from the upper end of the bed No.1 and the solution flown out from the lower end of the bed No.4 was obtained as a D-xylose solution. 6.0 minutes.

Second step: Water was supplied from the upper end of the bed No.3 and the solution flown out from the lower end of the bed No.4 was obtained as a D-xylose solution. 5.5 minutes.

Third step: The solution flown out from the lower end of the bed No.4 was sent to the upper end of the bed No.1 using a pump so that the solution in the inner side was moved in a circulating manner. 20 minutes.

Fourth step: Water was supplied from the upper end of the bed No.1 and the solution flown out from the lower end of the bed No.4 was obtained as an L-arabinose solution. 14.5 minutes.

Fifth step: Water was supplied from the upper end of the bed No.1 and the solution flown out from the lower end of the bed No.4 was obtained as an oligosaccharide solution. 21 minutes.

Sixth step: The solution flown out from the lower end of the bed No.4 was sent to the upper end of the bed No.1 using a pump so that the solution in the inner side was moved in a circulating manner. 9 minutes.

The supplying flow rate in each step (flow rate of the liquid sent by a pump in the third and the sixth steps) was 600 ml/hr. Accordingly, about 6.83-fold of water was supplied to the feedstock solution. Both of the feedstock solution and water were supplied at 65° C. Composition of the supplied feedstock solution and composition of each of the obtained solutions are shown in Table 3.

TABLE 3

| | Composition (% by weight) | | | |
|---|---|---|---|---|
| | Feedstock Solution | L-Arabinose Solution | D-Xylose Solution | Oligosaccharide Solution |
| L-Arabinose | 30.2 | 90.8 | 22.8 | 2.9 |
| D-Xylose | 14.0 | 3.8 | 56.1 | 0.1 |
| Glucose | 2.5 | 0.0 | 6.4 | 2.0 |
| Oligosaccharide | 53.3 | 5.4 | 14.7 | 95.0 |
| Concn of Solid (wt %) | 60.0 | 8.0 | 8.9 | 10.7 |

EXAMPLE 3

The same operation as in Example 2 was carried out except that the feedstock solution of Table 5 was used and that the time for each step was changed as shown in Table 4 whereupon an L-arabinose solution, a D-xylose solution and an oligosaccharide solution were prepared from the feedstock solution. The supplying rate of water to the feedstock solution was about 6.58-fold. The result is shown in Table 5.

TABLE 4

| Step | Time (minutes) |
|---|---|
| 1 | 6.0 |
| 2 | 4.0 |
| 3 | 22.2 |
| 4 | 15.0 |
| 5 | 20.5 |
| 6 | 9.0 |

TABLE 5

| | Composition (% by weight) | | | |
|---|---|---|---|---|
| | Feedstock Solution | L-Arabinase Solution | D-Xylose Solution | Oligosaccharide Solution |
| L-Arabinose | 28.0 | 91.0 | 9.6 | 6.4 |
| D-Xylose | 52.9 | 7.8 | 81.4 | 7.7 |
| Glucose | 12.6 | 0.1 | 8.6 | 47.7 |
| Oligosaccharide | 6.5 | 1.2 | 0.4 | 38.5 |
| Concn of Solid (wt %) | 60.0 | 6.9 | 25.5 | 3.4 |

What is claimed is:

1. A method for the purification of a saccharide, characterized in that, water and a feedstock solution containing at least L-arabinose and oligosaccharide where L-arabinose and/or xylose are/is the constituting component(s) obtained by hydrolysis of plant tissues are supplied to a chromatographic apparatus of a simulated moving-bed system where a solution can be circulated in one direction in an apparatus equipped with a packed bed in which an adsorbent including an acidic cation-exchange resin of a salt form is filled and the solution in the packed bed is moved in one direction whereupon at least L-arabinose and oligosaccharide are separated each other and concentration distribution of each of them is formed in the packed bed, then at least a concentrated L-arabinose solution and a concentrated oligosaccharide solution are extracted from the packed bed and, in addition, an inlet for the feedstock solution, an inlet for water, an outlet for the concentrated L-arabinose solution and an outlet for the concentrated oligosaccharide solution are successively shifted to the downstream inlets or outlets along the flowing direction of the solution.

2. A method for the purification of a saccharide, characterized in that, the following two steps are carried out for a chromatographic apparatus of a simulated moving-bed system where a solution is able to be circulated in one direction in a packed bed filled with an adsorbent including an acidic cation-exchange resin of a salt form and the inside of the packed bed is separated into an adsorption zone, a purification zone, a desorption zone and a concentration zone according to their functions A: a supplying and extracting step where a feedstock solution containing at least L-arabinose and an oligosaccharide where L-arabinose and/or xylose are/is the constituting component(s) obtained by hydrolysis of plant tissues is supplied to the upper part of the adsorption zone while water is supplied to the upper part of the desorption zone and at least a part of the solution flown down from the lower part of the desorption zone is extracted as a concentrated L-arabinose solution while all of the solution flown down from the lower part of the adsorption zone is extracted as a concentrated oligosaccharide solution and B: a circulating step where the solution in the packed bed is moved downstream in a circulating manner without supplying of the feedstock solution and water to the packed bed and without extracting of the solution from the packed bed and then the inlets and outlets are shifted to the corresponding downstream inlets and outlets without changing the relation of their relative positions whereby the above steps are repeated.

3. In a method for the purification of a saccharide where water and a feedstock solution containing L-arabinose, D-xylose and oligosaccharide where L-arabinose and/or xylose are/is the constituting component(s) obtained by hydrolysis of plant tissues are supplied to a chromatographic apparatus of a simulated moving-bed system where a solution can be circulated in one direction in an apparatus equipped with a packed bed in which an adsorbent including an acidic cation-exchange resin of a salt form is filled and the solution in the packed bed is moved in one direction whereupon L-arabinose, D-xylose and oligosaccharide are separated each other and concentration distribution of each of them is formed in the packed bed, and then a concentrated L-arabinose solution, a concentrated D-xylose solution and a concentrated oligosaccharide solution are extracted from the packed bed, the method which is characterized in that a process which comprises the following three steps A–C is repeated:

A: a step of supplying the feedstock solution where the feedstock solution is supplied from an inlet for the feedstock solution to move the solution in the packed bed downstream and all of the solution arriving at the position of the outlet for a D-xylose solution is extracted as a concentrated D-xylose solution;

B: a circulation step where the solution in the packed bed is moved downstream in a circulating manner without carrying out supplying to and extracting from the packed bed; and C: a desorption step where an operation comprising the following substeps is repeated by shifting an inlet for water, an outlet for a concentrated L-arabinose solution and an outlet for a concentrated D-xylose solution successively to the downstream inlet and outlets (a) a desorption substep where water is supplied from the inlet for water to move a solution in the packed bed downstream and a concentrated L-arabinose solution and a concentrated oligosaccharide solution are extracted from each of the outlets and (b) a circulation substep where the solution in the packed bed is moved downstream in a circulating manner without supplying and extracting.

4. The method for the purification of a saccharide according to claim 1, wherein the packed bed comprises 4–8 unit packed beds connected in series and each of the unit packed beds has a supplying means for the liquid at its upper part and an extracting means for the liquid at its lower part.

5. In a method for the purification of a saccharide where water and a feedstock solution containing L-arabinose, D-xylose and oligosaccharide where L-arabinose and/or xylose are/is the constituting component(s) obtained by hydrolysis of plant tissues are supplied to a chromatographic apparatus of a simulated moving-bed system where a solution can be circulated in one direction in an apparatus equipped with a packed bed in which an adsorbent including an acidic cation-exchange resin of a salt form is filled and the solution in the packed bed is moved in one direction by means of a connection of the frond end with the rear end by a pass for the solution whereupon L-arabinose, D-xylose and oligosaccharide are separated each other and concentration distribution of each of them is formed in the packed bed, and then a concentrated L-arabinose solution, a concentrated D-xylose solution and a concentrated oligosaccharide solution are extracted from the packed bed, the method which is characterized in that a process which at least comprises the following four steps A–D is repeated:

A: a supplying step where the feedstock solution is supplied from the front end of the packed bed and a concentrated D-xylose solution is extracted from the rear end of the packed bed;

B: a first circulation step where the solution in the packed bed is moved in a circulating manner without carrying out the supplying to the packed bed and the extracting from the packed bed;

C: a desorption step where water is supplied from the front end of the packed bed and, from the rear end of the packed bed, a concentrated L-arabinose solution and a concentrated oligosaccharide solution are extracted in this order; and D: a second circulation step where the solution in the packed bed is moved in a circulating manner without carrying out the supplying to the packed bed and the extracting from the packed bed.

6. The method for the purification of a saccharide according to claim 5, wherein an additional step where, after the supplying, water is supplied from the middle of the packed bed so that a concentrated D-xylose solution is extracted from the rear end thereof is carried out.

7. The method for the purification of a saccharide according to any of claims 1–6, wherein the absorbent is an alkaline earth metal salt of a strongly acidic cation-exchange resin of a gel type.

8. The method for the purification of a saccharide according to claim 1, wherein the ratio of L-arabinose occupying in the monosaccharide in the feedstock solution is 50% by weight or more.

9. The method for the purification of a saccharide according to claim 1, wherein the purity of L-arabinose occupying in the concentrated L-arabinose solution is at least 75% by weight.

10. The method for the purification of a saccharide according to claim 1, wherein the purity of L-arabinose occupying in the concentrated L-arabinose solution is 90% by weight or more.

11. The method for the purification of a saccharide according to claim 3, wherein the purity of D-xylose occupying in the concentrated D-xylose solution is at least 70% by weight.

12. The method for the purification of a saccharide according to claim 3, wherein the purity of D-xylose occupying in the concentrated D-xylose solution is 80% by weight or more.

13. The method for the purification of a saccharide according to claim 1, wherein the purity of oligosaccharide occupying in the concentrated oligosaccharide solution is at least 75% by weight.

14. The method for the purification of a saccharide according to claim 1, wherein the purity of oligosaccharide occupying in the concentrated oligosaccharide solution is 90% by weight or more.

15. The method of claim 1, wherein the absorbent is a sulfonated styrene-divinylbenzene cross-linking copolymer.

16. The method of claim 1, further comprising desalting the feedstock solution before supplying the solution to the chromatographic apparatus.

* * * * *